(12) United States Patent
Zou et al.

(10) Patent No.: US 9,347,029 B2
(45) Date of Patent: May 24, 2016

(54) MULTI-SENSOR BASED AUTOMATIC BREWING MASS OVERTURN MACHINE

(71) Applicant: JIANGSU UNIVERSITY, Zhenjiang, Jiangsu (CN)

(72) Inventors: Xiaobo Zou, Jiangsu (CN); Jiyong Shi, Jiangsu (CN); Jiewen Zhao, Jiangsu (CN); Zongbao Sun, Jiangsu (CN); Rong Xia, Jiangsu (CN); Leliu Sun, Jiangsu (CN); Xiaowei Huang, Jiangsu (CN); Xingyi Huang, Jiangsu (CN); Jianrong Cai, Jiangsu (CN); Quansheng Chen, Jiangsu (CN); Hao Lin, Jiangsu (CN)

(73) Assignee: JIANGSU UNIVERSITY (CN)

( * ) Notice: Subject to any disclaimer, the term of this patent is extended or adjusted under 35 U.S.C. 154(b) by 263 days.

(21) Appl. No.: 14/004,703

(22) PCT Filed: Nov. 28, 2012

(86) PCT No.: PCT/CN2012/085449
§ 371 (c)(1),
(2) Date: Sep. 12, 2013

(87) PCT Pub. No.: WO2014/032368
PCT Pub. Date: Mar. 6, 2014

(65) Prior Publication Data
US 2014/0245896 A1     Sep. 4, 2014

(30) Foreign Application Priority Data
Sep. 3, 2012  (CN) .......................... 2012 1 0318907

(51) Int. Cl.
| | | |
|---|---|---|
| *A23F 3/00* | (2006.01) |
| *C12J 1/10* | (2006.01) |
| *C12M 1/34* | (2006.01) |
| *C12M 1/36* | (2006.01) |

(52) U.S. Cl.
CPC . *C12J 1/10* (2013.01); *C12M 41/32* (2013.01); *C12M 41/48* (2013.01)

(58) Field of Classification Search
CPC ........... C12J 1/10; C12M 41/32; C12M 41/48
USPC .......... 99/323.12, 325, 329 R, 329 P, 329 RT, 99/356, 360–367, 371, 374, 377, 386, 99/443 R, 443 C
See application file for complete search history.

(56) References Cited

U.S. PATENT DOCUMENTS

| | | | | |
|---|---|---|---|---|
| 4,654,215 A | * | 3/1987 | Yamada | C12J 1/10 426/17 |
| 4,773,315 A | * | 9/1988 | Enenkel | C12J 1/10 99/277 |
| 5,290,701 A | * | 3/1994 | Wilkins | C12Q 1/02 382/133 |
| 2002/0164653 A1 | * | 11/2002 | Downs | C12M 23/08 435/7.1 |
| 2005/0118703 A1 | * | 6/2005 | Su | C12M 41/48 435/286.1 |
| 2012/0058534 A1 | * | 3/2012 | Stover | C02F 3/286 435/167 |

FOREIGN PATENT DOCUMENTS

| | | |
|---|---|---|
| CN | ZL94226760.5 | 10/1994 |
| CN | ZL02216018.3 | 12/2001 |
| CN | 2870474 Y  * | 2/2007 |
| CN | ZL200520076229.X | 2/2007 |
| CN | ZL200520076230.2 | 2/2007 |

OTHER PUBLICATIONS

CN2870474Y.pdf; CN2870474Y_translation.pdf.*

* cited by examiner

*Primary Examiner* — Dana Ross
*Assistant Examiner* — Ket D Dang
(74) *Attorney, Agent, or Firm* — Schmeiser, Olsen & Watts, LLP

(57) ABSTRACT

A multi-sensor based automatic brewing mass overturn machine comprising a moving module, a vinegar brewing mass information monitoring module, a system control module and a brewing mass overturn execution module is provided. The moving module comprises a moving motor, and the vinegar brewing mass information monitoring module comprises a vinegar brewing mass temperature and acidity information monitoring unit, a vinegar brewing mass smell information monitoring unit, and an overturned brewing mass appearance information monitoring unit. The system control module comprises a computer and a programmable controller, the computer being connected with a temperature sensor, an acidity sensor, a gas sensor array, a color camera and the programmable controller, respectively. The brewing mass overturn execution module comprises an overturn motor and brewing mass overturn motors.

9 Claims, 1 Drawing Sheet

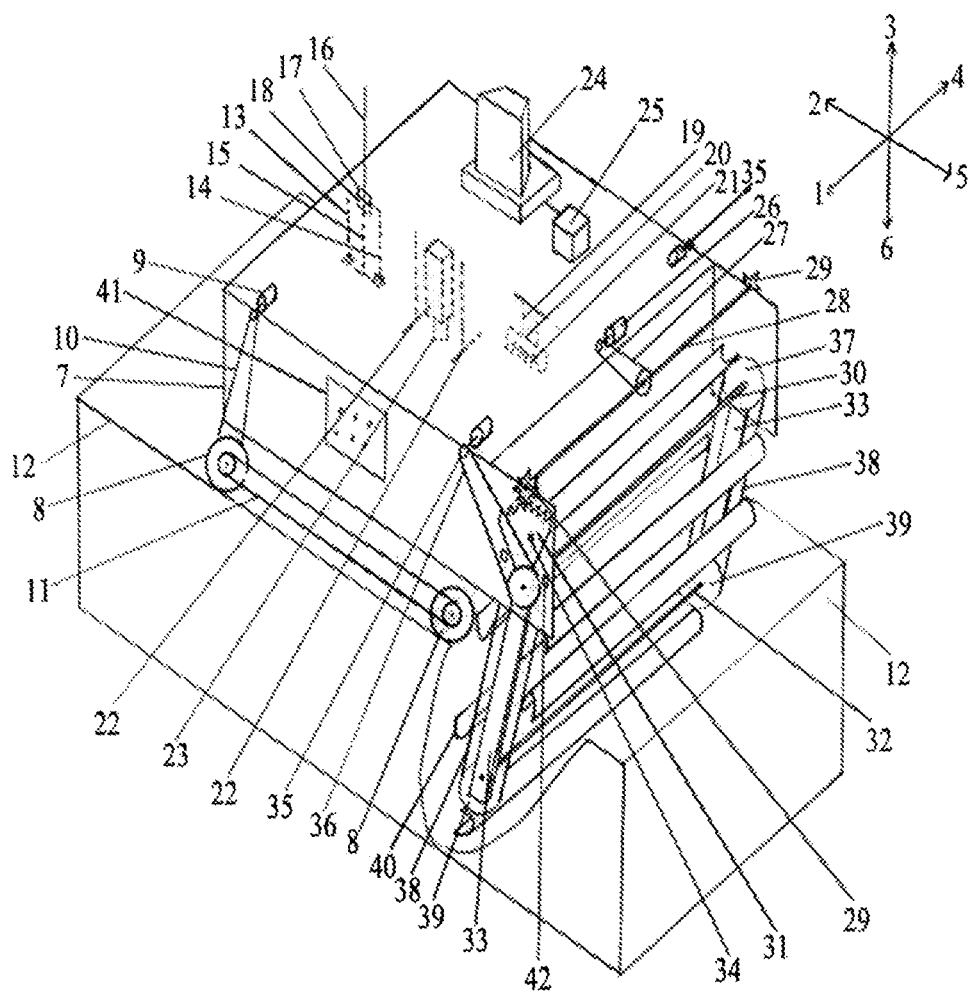

US 9,347,029 B2

MULTI-SENSOR BASED AUTOMATIC BREWING MASS OVERTURN MACHINE

FIELD OF TECHNOLOGY

The invention relates to a vinegar brewing equipment, i.e., a brewing mass overturn machine used in the industry of vinegar brewing.

BACKGROUND

There are two vinegar production processes, including solid-state fermentation and liquid-state fermentation, of which the solid-state fermentation has been widely applied due to pure taste of vinegar products and simple process. The solid-state fermentation is characterized in that the materials (brewing mass) are in solid state during the acetic fermentation, and alcohol is oxidized to acetic acid and other flavor substances by acetic bacteria and other microorganisms in the brewing mass during the fermentation. The reproduction and fermentation of acetic bacteria propose high requirements on temperature, acidity, oxygen content and etc. in the growth environment. Therefore, the acetic bacteria often realize reproduction in a part of the brewing mass with appropriate growth environment and are active in fermentation to result in the rising of temperature of the brewing mass. To make the entire brewing mass fermented uniformly and to keep the temperature of the brewing mass within an appropriate range, the brewing mass needs to be overturned.

Acetic fermentation in conventional solid-state fermentation vinegar production processes is carried out in unit of vinegar jars. Overturning the brewing mass (also known as "jar overturn") is mostly manual and empirical, with high labor intensity and poor working conditions. In the 1990s, the solid-state fermentation vinegar production processes were improved to replace vinegar jars with vinegar pools ("replacement of jars with pools") and replace manual brewing mass overturn with brewing mass overturn machines. The existing brewing mass overturn machines have a common structure that a hopper moves into a brewing mass pool to fill itself with the brewing mass under the drive of a transmission chain and then lifts up as it moves along with the chain, and the hopper makes its mouth face downward when it moves to the other side so that the brewing mass in the hopper falls back to the brewing mass pool due to gravity. The mechanical brewing mass overturn process is thus realized. The following relevant published patent documents have been already known: Patent No. ZL94226760.5, titled "Brewing Mass Overturn Machine"; Patent No. ZL02216018.3, titled "Brewing Mass Overturn Machine"; Patent No. ZL200520076229.X, titled "Light Brewing Mass Overturn Machine"; and, Patent No. ZL200520076230.2, titled "Brewing Mass Overturn and Discharging Machine". For such brewing mass overturn machines, although the replacement of manual brewing mass overturn with mechanical brewing mass overturn greatly decreases the labor intensity and improves the production efficiency, such brewing mass overturn machines are still reliant on manual operation and control, i.e., time, frequency, depth and other conditions of brewing mass overturn are determined upon what the workers see and what they smell in combination with their subjective experience. This lacks scientific support. Although the temperature, acidity, smell, color and other parameters of the brewing mass may be detected by physical and chemical analysis during the fermentation of the brewing mass to determine whether or not a brewing mass overturn operation is needed, it is always costly and laborious; furthermore, the detection points are too limited to realize overall monitoring.

SUMMARY

A multi-sensor based automatic brewing mass overturn machine, in order to overcome the deficiency that the existing brewing mass overturn machines require manual operation and control. The multi-sensor based automatic brewing mass overturn machine is able to automatically monitor information about temperature, acidity, appearance and smell of the brewing mass, and automatically execute brewing mass overturn actions according to the monitored information and preset thresholds.

The invention employs the following technical solutions. The multi-sensor based automatic brewing mass overturn machine comprises a moving module, a vinegar brewing mass information monitoring module, a system control module and a brewing mass overturn execution module. The moving module comprises a rack, four moving wheels disposed in front and rear rows below the rack and a moving motor located on top of the rack. A first moving chain wheel pair is provided between the moving motor and the moving wheel disposed at the left end of the front row below the rack. A second moving chain wheel pair is provided between two moving wheels in the front row. Two moving wheels in the front row move on the front edge of a brewing mass pool, while two moving wheels in the rear row move on the rear edge of the brewing mass pool. The vinegar information monitoring module comprises a vinegar brewing mass temperature and acidity information monitoring unit, a vinegar brewing mass smell information monitoring unit and an overturned brewing mass appearance information monitoring unit, which are in turn arrayed equidistantly from left to right along a front-rear symmetry axis on an upper surface of the rack. The brewing mass temperature and acidity information monitoring unit comprises a temperature sensor and an acidity sensor. The brewing mass smell information monitoring unit comprises a gas sensor array consisting of a plurality of different gas sensors. The overturned brewing mass appearance information monitoring unit comprises a color camera. The system control module comprises a computer and a programmable controller, which are fixed on the upper surface of the rack, the computer being connected with the temperature sensor, the acidity sensor, the gas sensor array, the color camera and the programmable controller via data lines, respectively. The brewing mass overturn execution module comprises an overturn motor that is fixed on the upper surface of the rack and connected with an overturn transmission shaft via an overturn chain wheel pair. The overturn transmission shaft is fixed on the upper surface of the rack and disposed axially in the front-rear direction. Two ends of the overturn transmission shaft are fixed with a transmission gear, respectively. The two transmission gears are in meshed transmission with two cluster gears, respectively. The two cluster gears are movably sleeved on two ends of a main shaft. Upper parts of two parallel overturn frames are also movably sleeved on the two ends of the main shaft, while lower parts thereof are fixedly connected with two ends of an auxiliary shaft. Two positioning clamps are fixedly connected with the two cluster gears at the corresponding ends, respectively, and clamped at the upper ends of the overturn frames at the corresponding ends. Two brewing mass overturn motors are fixed at front and rear positions on the upper surface of the rack and connected with the main shaft via corresponding overturn chain wheel pairs, respectively. Lower ends of the overturn frames are fixed with the auxiliary shaft parallel to the main shaft. An upper chain wheel group is close to insides of the overturn frames and fixed at two ends of the main shaft. A lower chain wheel group is close to insides of the overturn frames and sleeved at two ends of the auxiliary shaft. The upper chain wheel group is connected with the lower chain wheel group via a chain group. A brewing mass overturn hopper group parallel to the main shaft is fixed on the chain group. The rack on left and right sides of the cluster gears is provided with limiting columns for limiting the ultimate overturn angle of the overturn frames. The programmable controller is connected with the moving motor, the overturn motor and the brewing mass overturn motors via data lines, respectively. The brewing mass information monitoring module simultaneously acquires information about temperature, acidity, appearance and gas of the brewing mass at different positions of the brewing mass pool, and sends information values to the computer to be compared with brewing mass overturn thresholds stored therein in advance. When the information values reach the thresholds, the computer sends an instruction to the brewing mass overturn execution module to execute a brewing mass overturn action.

The invention has the following advantages: multiple sensors are used for automatically monitoring information about the vinegar brewing mass, including acquiring information about temperature of the brewing mass at different depths via a temperature sensor, acquiring information about acidity of the brewing mass at different depths via an acidity sensor, acquiring information about appearance of the brewing mass at different depths via a color camera, and acquiring information about smell of the brewing mass at different depths via a gas sensor array; and the system control module of the brewing mass overturn machine compares the monitored information of the brewing mass with preset thresholds, and sends a brewing mass overturn instruction to the brewing mass overturn execution module when the monitored information of the brewing mass reaches the preset thresholds. The automatic brewing mass information monitoring function of the automatic brewing mass overturn machine replaces the process of manual sense judgment or physical and chemical analysis on the state of the brewing mass, so that the state information of the brewing mass can be real-time acquired on line and automatically. Meanwhile, the automatic control module of the brewing mass overturn machine replaces the process of manual control of the brewing mass overturn machine, so that the brewing mass overturn process moves towards intelligent and information-based control from mechanic al control.

BRIEF DESCRIPTION

FIG. 1 is a structure diagram of the invention; and in the figure: 1, 2, 3, 4, 5, 6—Arrows; 7—Rack; 8—Moving wheels; 9—Moving motor; 10—First moving chain wheel pair; 11—Second moving chain wheel pair; 12—Brewing mass pool; 13—Temperature sensor; 14—Acidity sensor; 15—Protection arm; 16—Screw stem; 17—First positioning nut; 18—Second positioning nut; 19—Support columns; 20—Hollow glass tube; 21—Gas sensor array; 22—LED light sources; 23—Color camera; 24—Computer; 25—Programmable controller; 26—Overturn motor; 27—Overturn chain wheel pair; 28—Overturn transmission shaft; 29—Transmission gears; 30—Main shaft; 31—Cluster gears; 32—Auxiliary shaft; 33—Overturn frames; 34—Positioning clamps; 35—Brewing mass overturn motors; 36—Brewing mass overturn chain wheel pairs; 37—Upper chain wheel group; 38—Chain group; 39—Lower chain wheel group; 40—Hopper group; 41—Electric control boxes; and, 42—Limiting columns.

DETAILED DESCRIPTION

The multi-sensor based automatic brewing mass overturn machine comprises a moving module, a vinegar brewing mass information monitoring module, a system control module and a brewing mass overturn execution module. FIG. 1 is a structure diagram of the multi-sensor based automatic brewing mass overturn machine, in which, Arrow 1 indicates the front direction, Arrow 2 indicates the right direction, Arrow 3 indicates the up direction, Arrow 4 indicates the rear direction, Arrow 5 indicates the left direction, and Arrow 6 indicates the down direction.

The moving module comprises a rack 7 located above a brewing mass pool 12, four moving wheels 8 disposed in front and rear rows below the rack 7 and a moving motor 9 located on top of the rack 7, a first moving chain wheel pair 10 being provided between the moving motor 9 and the moving wheel 8 disposed at the left end of the front row below the rack 7, a second moving chain wheel pair 11 being provided between two moving wheels 8 in the front row, wherein the rack 7 looks like a rectangular solid, the front, rear, left, right and upper faces of which are sealed by stainless steel plates; and the two moving wheels 8 in the front row of the rack 7 move on the front edge of the brewing mass pool 12, while the two moving wheels in the rear row of the rack 7 move on the rear edge of the brewing mass pool 12.

The vinegar information monitoring module comprises a vinegar brewing mass temperature and acidity information monitoring unit, a vinegar brewing mass smell information monitoring unit and an overturned brewing mass appearance information monitoring unit, which are in turn arrayed equidistantly from left to right along a front-rear symmetry axis of an upper surface of the rack 7.

The brewing mass temperature and acidity information monitoring unit comprises a temperature sensor 13, an acidity sensor 14, a protection arm 15, a screw stem 16, a first positioning nut 17 and a second positioning nut 18, wherein the temperature sensor 13, the protection arm 15 and the acidity sensor 14 are in turn arrayed equidistantly from left to right and fixedly connected with the screw stem 16, respectively; the screw stem 16 is vertical to the upper surface of the rack 17 from up to down and sleeved on the upper surface of the rack 7; and the screw stem 16 is sleeved on the rack 7 via the first positioning nut 17 located above the upper surface of the rack 7 and the second positioning nut 18 located below the upper surface of the rack 7, respectively. When the first positioning nut 17, the screw stem 16 and the second positioning nut 18 are tightened with each other, the brewing mass temperature and acidity information monitoring unit may be fixed on the rack 7, and the depths that the temperature sensor 13 and the acidity sensor 14 are inserted into the brewing mass pool 12 may be adjusted by adjusting positions of the first positioning nut 17 and the second positioning nut 18 on the screw stem 16. The temperature sensor 13 and the acidity sensor 14 are connected with the computer 24 via data lines to feed back information about temperature and acidity of the brewing mass to the computer 24.

The brewing mass smell information monitoring unit comprises two support columns 19 fixed below the upper surface of the rack 7, a hollow glass tube 20 fixed at the lower ends of the support columns 19, and a gas sensor array 21 located inside the hollow glass tube 20 and consisting of a plurality of different gas sensors. The gas sensor array 21 is connected with the computer 24. The gas sensor array 21 is able to monitor smell information in the surface air of the brewing mass and feed back the smell information of the brewing mass to the computer 24 via a data line.

The overturned brewing mass appearance information monitoring unit comprises two strip-shaped LED light sources 22 fixed below the upper surface of the rack 7, and a color camera 23 fixed below the upper surface of the rack 7 with a lens thereof vertical to the brewing mass pool 12. The color camera 23 is connected with the computer 24. From left to right, the color camera 23 is located between the two LED light sources 22, and the LED light sources 22 and the color camera 23 are arrayed equidistantly from left to right. The two strip-shaped LED light sources 22 are erected in the front-rear direction. The color camera 23 feeds back the appearance information of the brewing mass to the computer via a data line.

The system control module comprises the computer 24 and a programmable controller 25 fixed on the upper surface of the rack 7. The computer 24 is connected with the temperature sensor 13, the acidity sensor 14, the gas sensor array 21, the color camera 23 and the programmable controller 25 via data lines, respectively. The programmable controller 25 is connected with the moving motor 9, the overturn motor 26 and the brewing mass overturn motors 35 via data lines, respectively. The computer 24 may store information about the brewing mass acquired by the brewing mass information monitoring module, and control the brewing mass overturn execution module to execute a brewing mass overturn action via the programmable controller 25 according to the thresholds preset in the computer 24.

The brewing mass overturn execution module comprises an overturn motor 26, an overturn chain wheel pair 27, an overturn transmission shaft 28, transmission gears 29, a main shaft 30, cluster gears 31, an auxiliary shaft 32, overturn frames 33, positioning clamps 34, brewing mass overturn motors 35, brewing mass overturn chain wheel pairs 36, an upper chain wheel group 37, a chain group 38, a lower chain wheel group 39, a brewing mass overturn hopper group 40 and limiting columns 42. The overturn motor 26 is fixed on the upper surface of the rack 7 and connected with the overturn transmission shaft 28 via the overturn chain wheel pair 27. The overturn transmission shaft 28 is fixed on the upper surface of the rack and disposed axially in the front-rear direction. Two ends of the overturn transmission shaft 28 are fixed with a transmission gear 29, respectively. The two transmission gears 29 at the two ends are in meshed transmission with two cluster gears 31, respectively. The two cluster gears 31 are movably sleeved on two ends of the main shaft 30. Upper parts of two overturn frames 33 are also movably sleeved on two ends of the main shaft 30, while lower ends thereof are fixedly connected with two ends of the auxiliary shaft 32. The two overturn frames 33 are parallel to each other from front to rear. Two positioning claims 34 are fixedly connected with the two cluster gears 31 at the corresponding ends, respectively, and clamped at the upper ends of the overturn frames 33 at the corresponding ends. Two brewing mass overturn motors 35 are fixed at front and rear positions on the upper surface of the rack 7 and connected with the main shaft 30 via the corresponding overturn chain wheel pairs 36, respectively. Lower ends of the overturn frames 33 are fixed with the auxiliary shaft 32 parallel to the main shaft 30. The upper chain wheel group 37 is close to insides of the overturn frames 33 and fixed at two ends of the main shaft 30. The lower chain wheel group 39 is close to insides of the overturn frames 33 and sleeved at two ends of the auxiliary shaft 32. The upper chain wheel group 37 is connected with the lower chain wheel group 39 via the chain group 38. The brewing mass overturn hopper group 40 parallel to the main shaft 30 is fixed on the chain group 38. The rack 7 on left and right sides of the cluster gears 31 are designed with limiting columns 42 for limiting the ultimate overturn angle of the overturn frames 33.

On both sides of the rack 7, electric control boxes 41 connected with the moving motor 9, the overturn motor 26, the brewing mass overturn motors 35 and the computer 24, respectively, are designed.

The two cluster gears 31 both form sectors with an angle of 75-90°. Curved sides of the sectors are provided with gears meshed with the gears 29. The centers of the sectors are movably sleeved on two ends of the main shaft 30 and fixedly connected with upper ends of the two overturn frames 33 via the positioning clamps 34.

The upper chain wheel group 37 and the lower chain wheel group 39 at least consist of four chain wheels corresponding to each other from up to down.

The moving motor 9, the overturn motor 26 and the brewing mass overturn motors 35 all are low speed motors or common motors equipped with reducers and turbine reduction self-locking devices.

The working flow of the automatic brewing mass overturn machine provided by the invention is as below. When the brewing mass overturn machine enters to the working state, the computer 24 in the system control module sends an instruction to the moving module and the brewing mass information monitoring module. The moving module controls the brewing mass overturn machine to move along the edge of the brewing mass pool 12 to different positions of the brewing mass pool 12, while the brewing mass information monitoring module simultaneously acquires information about temperature, acidity, appearance and smell of the brewing mass at different positions of the brewing mass pool. The information fed back by the brewing mass information monitoring module is sent to the computer 24 and the information values are compared with brewing mass overturn thresholds stored in the computer 24 in advance. When the information values fed back by the brewing mass information monitoring module reach the preset brewing mass overturn thresholds, the computer 24 sends an instruction to the brewing mass overturn execution module to control the brewing mass overturn execution module to execute a brewing mass overturn action.

When the brewing mass overturn action is executed, the computer 24 sends a running instruction to the overturn motor 26 via the programmable controller 25, and controls the cluster gears 31, the positioning clamps 34, the overturn frames 33, the upper chain wheel group 37, the chain group 38, the lower chain wheel group 39 and the hopper group 40 to incline rightward to a working angle through the transmissions of the overturn motor 26, the overturn chain wheel pair 27, the overturn transmission shaft 28, the transmission gears 29 and the cluster gears 31 in turn. The brewing mass above the depth corresponding to this working angle is the object of brewing mass overturn operation of the hopper group 40. At this moment, the overturn motor 26 is locked so that the working angle is fixed. Subsequently, the computer 24 sends a running instruction to the brewing mass overturn motors 35 via the programmable controller 25, and controls the hopper 40 fixed on the chain group 38 to fill the brewing mass into the hopper on the left of the overturn frames 33 through the transmissions of the brewing mass overturn motors 35, the brewing mass overturn chain wheel pairs 36, the main shaft 30, the upper chain wheel group 37, the chain group 38 and the lower chain wheel group 39 in turn. When the brewing mass in the hopper 40 is lifted up to the right side of the overturn frames 33, the mouth of the hopper 40 turns to face downward, and the brewing mass in the hopper 40 falls back to the brewing mass pool 12 due to gravity, thereby realizing one time of overturn action to the brewing mass. While the brewing mass overturn execution module is executing the brewing mass overturn action, the moving module controls the brewing mass overturn machine to move continuously along the edge of the brewing mass pool 12, thus to realize overturn to the brewing mass in the whole brewing mass pool 12.

After the brewing mass in the whole brewing mass pool is overturned once, the brewing mass overturn execution module stops working. The computer 24 controls the brewing mass information monitoring module to continuously monitor information about temperature, acidity, appearance and smell of the brewing mass. When the information fed back reaches the preset thresholds, the system control module controls the brewing mass overturn machine to another brewing mass overturn action.

What is claimed is:

1. A multi-sensor based automatic brewing mass overturn machine comprising:
    a moving module, the moving module including a rack, four moving wheels disposed in a front row and a rear row below the rack such that there are two moving wheels in the front row and two moving wheels in the rear row, and moving motor located on a top of the rack, a first moving chain wheel pair being provided between the moving motor and a first front moving wheel disposed at a left end of the front row below the rack, a second moving chain wheel pair being provided between the two moving wheels in the front row, wherein the two moving wheels in the front row move on a front edge of a brewing mass pool, and the two moving wheels in the rear row move on a rear edge of the brewing mass pool;
    a vinegar brewing mass information monitoring module, the vinegar information monitoring module including a vinegar brewing mass temperature and acidity information monitoring unit, a vinegar brewing mass smell information monitoring unit and an overturned brewing mass appearance information monitoring unit, which are in turn arrayed equidistantly from left to right along a front-rear symmetry axis of an upper surface of the rack, wherein the brewing mass temperature and acidity information monitoring unit comprises a temperature sensor and an acidity sensor, the brewing mass smell information monitoring unit comprises a gas sensor array consisting of a plurality of different gas sensors, and the overturned brewing mass appearance information monitoring unit comprises a color camera;
    a system control module, the system control module including a computer and a programmable controller that are fixed on an upper surface of the rack, the computer being connected with the temperature sensor, the acidity sensor, the gas sensor array, the color camera, and the programmable controller via data lines; and
    a brewing mass overturn execution module, the brewing mass overturn execution module including an overturn motor that is fixed on the upper surface of the rack and connected with an overturn transmission shaft via an overturn chain wheel pair, the overturn transmission shaft being fixed on the upper surface of the rack and disposed axially in a front-rear direction, each end of the overturn transmission shaft being fixed with a transmission gear, such that there are two transmission gears, each of the two transmission gears being in meshed transmission with a cluster gear, such that there are two cluster gears, the two cluster gears being movably sleeved on opposite ends of a main shaft, wherein upper parts of two parallel overturn frames also being movably sleeved on the two ends of the main shaft, while lower parts thereof being fixedly connected with two ends of an auxiliary shaft, further wherein two positioning clamps are fixedly connected with the two cluster gears at corresponding ends, and being clamped at the upper ends of the overturn frames at the corresponding ends;
    wherein two brewing mass overturn motors are fixed at front and rear positions on the upper surface of the rack and connected with the main shaft via corresponding overturn chain wheel pairs, and lower ends of the overturn frames are fixed with the auxiliary shaft parallel to the main shaft, further wherein an upper chain wheel group is close to an inside of the overturn frames and fixed at two ends of the main shaft, a lower chain wheel group being close to the inside of the overturn frames and sleeved at two ends of the auxiliary shaft, the upper chain wheel group being connected with the lower chain wheel group via a chain group,
    wherein a brewing mass overturn hopper group parallel to the main shaft is fixed on the chain group, and the rack on left and right sides of the cluster gears are provided with limiting columns for the limiting an ultimate overturn angle of the overturn frames;
    wherein the programmable controller is connected with the moving motor, the overturn motor, and the brewing mass overturn motors via data lines;
    wherein the brewing mass information monitoring module simultaneously acquires information about temperature, acidity, appearance and smell of the brewing mass at different positions of the brewing mass pool, and sends information values to the computer to be compared with brewing mass overturn thresholds stored therein in advance, further wherein, when the information values reach the thresholds, the computer sends an instruction to the brewing mass overturn execution module to execute a brewing mass overturn action.

2. The automatic brewing mass overturn machine based on multiple sensors according to claim 1, wherein the brewing mass temperature and acidity information monitoring unit further comprises a protection arm, a screw stem, and first and second positioning nuts, further wherein the temperature sensor, the protection arm, and the acidity sensor are arrayed equidistantly from left to right and fixedly connected with the screw stem, and the screw stem being sleeved on the rack via the first positioning nut located above the upper surface of the rack and the second positioning nut located below the upper surface of the rack.

3. The automatic brewing mass overturn machine based on multiple sensors according to claim 1, wherein the brewing mass smell information monitoring unit further comprises two support columns fixed below the upper surface of the rack, and a hollow glass tube fixed at the lower ends of the support columns, and the gas sensor array is located inside the hollow glass tube.

4. The automatic brewing mass overturn machine based on multiple sensors according to claim 1, wherein the overturned brewing mass appearance information monitoring unit further comprises LED light sources fixed below the upper surface of the rack, and the color camera is fixed below the upper surface of the rack with a lens thereof vertical to the brewing mass pool.

5. The automatic brewing mass overturn machine based on multiple sensors according to claim 1, wherein, on both sides of the rack, electric control boxes connected with the moving motor, the overturn motor, the brewing mass overturn motors, and the computer are designed.

6. The automatic brewing mass overturn machine based on multiple sensors according to claim 1, wherein the cluster gears both form sectors with an angle of 75-90°, curved sides of the sectors being provided with gears meshed with the gears, the centers of the sectors being movably sleeved on two ends of the main shaft and fixedly connected with upper ends of the two overturn frames via the positioning clamps.

7. The automatic brewing mass overturn machine based on multiple sensors according to claim 1, wherein the upper chain wheel group and the lower chain wheel group at least consist of four chain wheels corresponding to each other from up to down.

8. The automatic brewing mass overturn machine based on multiple sensors according to claim 1, wherein the temperature sensor and the acidity sensor are inserted into the brewing mass pool when in use.

9. The automatic brewing mass overturn machine based on multiple sensors according to claim 8, wherein a depth at which the temperature sensor and the acidity sensor are inserted into the brewing mass pool is adjustable.

\* \* \* \* \*